United States Patent
Li et al.

(10) Patent No.: US 8,133,501 B2
(45) Date of Patent: Mar. 13, 2012

(54) IMPLANTABLE OR INSERTABLE MEDICAL DEVICES FOR CONTROLLED DRUG DELIVERY

(75) Inventors: Jianmin Li, Lexington, MA (US); Danielle Conley, Waltham, MA (US); Weenna Bucay Couto, Winchester, MA (US); Cang Duy Dao, Attleboro, MA (US); Hamid Davoudi, Westwood, MA (US); Raymond Lareau, Westford, MA (US); Kathleen M. Miller, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 976 days.

(21) Appl. No.: 10/377,131

(22) Filed: Feb. 28, 2003

(65) Prior Publication Data

US 2003/0224033 A1 Dec. 4, 2003

Related U.S. Application Data

(63) Continuation-in-part of application No. 10/209,476, filed on Jul. 31, 2002, and a continuation-in-part of application No. 10/071,840, filed on Feb. 8, 2002, now Pat. No. 6,887,270.

(51) Int. Cl.
*A61F 2/02* (2006.01)
(52) U.S. Cl. ...................................................... 424/425
(58) Field of Classification Search .................. None
See application file for complete search history.

(56) References Cited

U.S. PATENT DOCUMENTS

| | | | |
|---|---|---|---|
| 3,279,996 A | 10/1966 | Long, Jr. et al. |
| 3,618,604 A | 11/1971 | Ness |
| 3,832,252 A | 8/1974 | Higuchi et al. |
| 3,845,480 A | 10/1974 | Zaffaroni |
| 3,845,770 A | 11/1974 | Theeuwes et al. |

(Continued)

FOREIGN PATENT DOCUMENTS

DE 3347660 A1 7/1985

(Continued)

OTHER PUBLICATIONS

Theodorou C et al, Incontinence after surgery for benign prostatic hypertrophy: The case for complex approach and treatment. (abstract).*

(Continued)

*Primary Examiner* — Carlos Azpuru
(74) *Attorney, Agent, or Firm* — Mayer & Williams PC; David B. Bonham; Kevin J. Park

(57) ABSTRACT

Implantable or insertable medical devices are provided, which comprises: (a) a biocompatible polymer; and (b) at least one therapeutic agent selected from an anti-inflammatory agent, an analgesic agent, an anesthetic agent, and an antispasmodic agent. The medical devices are adapted for implantation or insertion at a site associated with pain or discomfort upon implantation or insertion. In many embodiments, the therapeutic will be selected from at least one of (i) ketorolac and pharmaceutically acceptable salts thereof (e.g., ketorolac tromethamine) and (ii) 4-diethylamino-2-butynylphenylcyclohexyl glycolate and pharmaceutically acceptable salts thereof (e.g., oxybutynin chloride). Also provided are uses for the implantable or insertable medical devices, which uses comprise reducing pain or discomfort accompanying the implantation or insertion of such devices. Further uses may comprise reducing microbial buildup along the device. Methods for manufacturing implantable or insertable medical devices are also provided.

23 Claims, 4 Drawing Sheets

U.S. PATENT DOCUMENTS

| | | | |
|---|---|---|---|
| 3,916,899 A | 11/1975 | Theeuwes et al. | |
| 3,948,254 A | 4/1976 | Zaffaroni | |
| 3,993,072 A | 11/1976 | Zaffaroni | |
| 4,036,227 A | 7/1977 | Zaffaroni et al. | 424/428 |
| 4,054,139 A | 10/1977 | Crossley | 128/260 |
| 4,069,307 A | 1/1978 | Higuchi et al. | |
| 4,111,202 A | 9/1978 | Theeuwes | |
| 4,186,745 A | 2/1980 | Lewis et al. | |
| 4,240,163 A | 12/1980 | Galin | 3/13 |
| 4,309,996 A | 1/1982 | Theeuwes | |
| 4,391,797 A | 7/1983 | Folkman et al. | |
| 4,472,327 A | 9/1984 | Neefe | 264/1.9 |
| 4,589,880 A | 5/1986 | Dunn et al. | |
| 4,603,152 A | 7/1986 | Laurin et al. | 604/265 |
| 4,723,950 A | 2/1988 | Lee | 604/322 |
| 4,731,080 A | 3/1988 | Galin | 623/6 |
| 4,816,264 A | 3/1989 | Phillips et al. | |
| 4,853,978 A | 8/1989 | Stockum | 2/167 |
| 4,902,503 A | 2/1990 | Umemura et al. | 424/83 |
| 4,923,450 A | 5/1990 | Maeda et al. | 604/265 |
| 4,933,178 A | 6/1990 | Capelli | |
| 4,946,899 A | 8/1990 | Kennedy et al. | 525/244 |
| 4,959,217 A | 9/1990 | Sanders et al. | |
| 4,973,304 A | 11/1990 | Graham et al. | |
| 4,978,391 A | 12/1990 | Jones | 106/35 |
| 5,080,892 A | 1/1992 | Yamamori et al. | 424/78.09 |
| 5,091,205 A | 2/1992 | Fan | 427/2 |
| 5,091,442 A | 2/1992 | Milner | 523/122 |
| 5,098,379 A | 3/1992 | Conway et al. | 604/51 |
| 5,102,401 A | 4/1992 | Lambert et al. | 604/264 |
| 5,102,402 A | 4/1992 | Dror et al. | 604/265 |
| 5,114,719 A | 5/1992 | Sabel et al. | |
| 5,130,159 A | 7/1992 | Shlenker et al. | 427/2 |
| 5,135,516 A | 8/1992 | Sahatjian et al. | 604/265 |
| 5,137,671 A | 8/1992 | Conway et al. | 264/130 |
| 5,165,952 A | 11/1992 | Solomon et al. | 427/2 |
| 5,171,318 A | 12/1992 | Gibson et al. | 623/5 |
| 5,178,870 A | 1/1993 | Schaeken et al. | 424/405 |
| 5,217,493 A | 6/1993 | Raad et al. | 623/11 |
| 5,261,896 A | 11/1993 | Conway et al. | 604/265 |
| 5,272,012 A | 12/1993 | Opolski | 428/423.1 |
| 5,279,594 A | 1/1994 | Jackson | |
| 5,282,784 A | 2/1994 | Willard | |
| 5,304,121 A | 4/1994 | Sahatjian | 604/53 |
| 5,316,774 A | 5/1994 | Eury et al. | |
| 5,328,954 A | 7/1994 | Sarangapani | 524/589 |
| 5,344,411 A | 9/1994 | Domb et al. | 604/265 |
| 5,360,415 A | 11/1994 | Yabushita et al. | 604/265 |
| 5,362,754 A | 11/1994 | Raad et al. | 514/566 |
| 5,366,505 A | 11/1994 | Farber | 623/11 |
| 5,370,681 A | 12/1994 | Herweck et al. | 623/1 |
| 5,378,475 A | 1/1995 | Smith et al. | |
| 5,389,314 A | 2/1995 | Wang | 264/25 |
| 5,409,012 A | 4/1995 | Sahatjian | 128/749 |
| 5,462,644 A | 10/1995 | Woodson | 204/131 |
| 5,468,787 A | 11/1995 | Braden et al. | 523/113 |
| 5,509,900 A | 4/1996 | Kirkman | 604/104 |
| 5,512,055 A | 4/1996 | Domb et al. | |
| 5,527,337 A | 6/1996 | Stack et al. | 606/198 |
| 5,569,463 A | 10/1996 | Helmus et al. | 424/426 |
| 5,599,298 A | 2/1997 | Sahatjian | 604/49 |
| 5,605,696 A | 2/1997 | Eury et al. | |
| 5,607,683 A | 3/1997 | Capelli | 424/405 |
| 5,611,354 A | 3/1997 | Alleyne | 128/846 |
| 5,616,119 A | 4/1997 | Davis | 604/19 |
| 5,616,608 A | 4/1997 | Kinsella et al. | 514/449 |
| 5,624,704 A | 4/1997 | Darouiche et al. | 427/2.24 |
| 5,629,008 A | 5/1997 | Lee | |
| 5,643,207 A | 7/1997 | Rise | 604/93 |
| 5,647,843 A | 7/1997 | Mesrobian et al. | |
| 5,656,296 A | 8/1997 | Khan et al. | |
| 5,676,972 A | 10/1997 | Galiatsatos et al. | |
| 5,679,399 A | 10/1997 | Shlenker et al. | 427/2.3 |
| 5,693,034 A | 12/1997 | Buscemi et al. | 604/265 |
| 5,697,967 A | 12/1997 | Dinh et al. | |
| 5,702,754 A | 12/1997 | Zhong | 427/2.12 |
| 5,707,366 A | 1/1998 | Solomon et al. | 604/265 |
| 5,716,406 A | 2/1998 | Farber | 623/11 |
| 5,741,331 A | 4/1998 | Pinchuk | 623/11 |
| 5,772,640 A | 6/1998 | Modak et al. | 604/265 |
| 5,849,327 A | 12/1998 | Berliner et al. | |
| 5,853,745 A | 12/1998 | Darouiche | 424/423 |
| 5,873,904 A | 2/1999 | Ragheb et al. | 623/1 |
| 5,877,224 A | 3/1999 | Brocchini et al. | |
| 5,902,283 A | 5/1999 | Darouiche et al. | 604/265 |
| 5,932,248 A | 8/1999 | Chen et al. | |
| 5,945,115 A | 8/1999 | Dunn et al. | |
| 5,989,463 A | 11/1999 | Tracy et al. | |
| 6,001,386 A | 12/1999 | Ashton et al. | |
| 6,013,853 A | 1/2000 | Athanasiou et al. | |
| 6,039,967 A | 3/2000 | Ottoboni et al. | |
| 6,060,534 A | 5/2000 | Ronan et al. | 523/113 |
| 6,083,208 A | 7/2000 | Modak et al. | 604/265 |
| 6,096,108 A | 8/2000 | Coulonvaux et al. | 55/385.3 |
| 6,106,505 A | 8/2000 | Modak et al. | 604/265 |
| 6,120,789 A | 9/2000 | Dunn | |
| 6,143,314 A | 11/2000 | Chandrashekar et al. | |
| 6,176,849 B1 | 1/2001 | Yang et al. | 604/265 |
| 6,179,817 B1 | 1/2001 | Zhong | |
| 6,184,266 B1 | 2/2001 | Ronan et al. | 523/113 |
| 6,224,579 B1 | 5/2001 | Modak et al. | 604/265 |
| 6,248,129 B1 | 6/2001 | Froix | |
| 6,258,121 B1 | 7/2001 | Yang et al. | |
| 6,261,630 B1 | 7/2001 | Nazarova et al. | 427/2.12 |
| 6,299,894 B1 | 10/2001 | Markkula et al. | |
| 6,316,522 B1 | 11/2001 | Loomis et al. | 523/105 |
| 6,322,847 B1 | 11/2001 | Zhong et al. | |
| 6,335,028 B1 | 1/2002 | Vogel et al. | |
| 6,335,029 B1 | 1/2002 | Kamath et al. | |
| 6,475,434 B1 | 11/2002 | Darouiche | 422/28 |
| 6,482,830 B1 | 11/2002 | Redkar et al. | 514/283 |
| 6,545,097 B2 | 4/2003 | Pinchuk et al. | 525/240 |
| 6,596,401 B1 | 7/2003 | Terry et al. | 428/447 |
| 6,641,831 B1 | 11/2003 | Schierholz | 424/422 |
| 6,706,024 B2 | 3/2004 | Modak et al. | 604/265 |
| 6,719,991 B2 | 4/2004 | Darouiche et al. | 424/422 |
| 6,746,481 B1 * | 6/2004 | Larik et al. | 623/1.45 |
| 6,796,960 B2 | 9/2004 | Cioanta et al. | 604/103.01 |
| 2001/0010016 A1 | 7/2001 | Modak et al. | 623/1.42 |
| 2002/0031601 A1 | 3/2002 | Darouiche et al. | 427/2.1 |
| 2002/0107330 A1 | 8/2002 | Pinchuk et al. | 525/242 |
| 2002/0165521 A1 | 11/2002 | Cioanta et al. | 604/509 |
| 2002/0188246 A1 | 12/2002 | Hayner et al. | |
| 2003/0018306 A1 | 1/2003 | Bucay-Couto et al. | 604/265 |
| 2003/0024534 A1 | 2/2003 | Silvestri et al. | 128/846 |
| 2003/0060877 A1 | 3/2003 | Falotico et al. | 623/1.42 |
| 2003/0078242 A1 | 4/2003 | Raad et al. | 514/150 |
| 2003/0153983 A1 | 8/2003 | Miller et al. | 623/23.7 |
| 2003/0199993 A1 | 10/2003 | Gellman et al. | 623/23.75 |
| 2003/0203991 A1 | 10/2003 | Schottman et al. | 523/334 |
| 2003/0224033 A1 | 12/2003 | Li et al. | 424/423 |
| 2004/0166094 A1 | 8/2004 | Darouiche et al. | 424/93.4 |
| 2004/0166102 A1 | 8/2004 | Darouiche et al. | 424/93.45 |
| 2004/0208908 A1 | 10/2004 | Modak et al. | 424/423 |
| 2004/0249441 A1 | 12/2004 | Miller et al. | 623/1.15 |

FOREIGN PATENT DOCUMENTS

| | | |
|---|---|---|
| EP | 0 328 421 A2 | 8/1989 |
| EP | 0 379 271 A2 | 7/1990 |
| EP | 0 734 721 A2 | 10/1996 |
| EP | 0 970 711 A2 * | 1/2000 |
| EP | 0970711 A2 | 1/2000 |
| EP | 0 970 711 A2 * | 12/2000 |
| EP | 1 247 537 A1 | 10/2002 |
| GB | 2152382 A | 8/1985 |
| GB | 2319507 A | 5/1998 |
| WO | WO 93/10847 | 6/1993 |
| WO | 95/06487 A2 | 3/1995 |
| WO | 95/08305 A1 | 3/1995 |
| WO | WO 97/14447 | 4/1997 |
| WO | WO 98/36784 | 8/1998 |
| WO | WO 99/24391 | 5/1999 |
| WO | WO 99/47595 | 9/1999 |
| WO | 00/62830 A2 | 10/2000 |
| WO | WO 01/03607 A2 | 1/2001 |
| WO | WO 01/21229 A1 | 3/2001 |

| | | |
|---|---|---|
| WO | WO 02/21913 A2 | 3/2002 |
| WO | WO 02/43788 | 6/2002 |
| WO | WO 03/066119 A1 | 8/2003 |

OTHER PUBLICATIONS

Theodorou C et al, "Incontinenece After Surgery for Benign Prostatic Hypertrophy: The Case for complex Approach and Treatment", (Abstract), 1998.*

Konety, Badrinath et. al, Urolume Stent Placement for the treatment of postbrachytherapy bladder outlet obstruction, Urology 55: 721-724, 2000.

Vasudev, Sindhu C. et. al., Development of chitosan/polyethylene vinyl acetate co-matrix: controlled release of aspirin-heparin for preventing cardiovascular thrombosis, Biomaterials, 1997, vol. 18 No. 5, pp. 375-381.

Olweny, Ephrem O. et al., Evaluation of a chronic indwelling prototype mesh ureteral stent in a porcine model, Urology 56 (5) 2000, pp. 857-862.

Gonzalez, Alex et. al., Minimizing Hospital Length of Stay in Chrildren Undergoing Ureteroneocystostomy, Urology 52 (3) 1998, pp. 501-504.

Ketorolac. The Merck Index. 14th Ed. Accessed online on Nov. 3, 2008 at http://themerckindex.cambridgesoft.com/TheMerckIndexlindex.asp.

Oxybutynin. The Merck Index. 14th Ed. Accessed online on Nov. 3, 2008 at http://themerckindex.cambridgesoft.com/TheMerckIndexlindex.asp.

Percuflex® Tail Plus™Tapered Ureteral Stent. Boston Scientific. Urology. http://www.bostonscientific.com/med_specialty/deviceDetail.jhtml?task=tskBasicDevice.jhtml&s. Feb. 24, 2004 download.

H.N. Bhargava et al., "Triclosan: Applications and Safety," *American Journal of Infection Control*, vol. 24(3), Jun. 1996, pp. 209-218.

Rhonda D. Jones et al., "Triclosan: A Review of Effectiveness and Safety in Health Care Settings," *American Journal of Infection Control*, vol. 28(2), Apr. 2000, pp. 184-196.

J. Regõs et al., "Antimicrobial Spectrum of Triclosan, a Broad-Spectrum Antimicrobial Agent for Topical Application. II. Comparison with Some Other Antimicrobial Agents," *Dermatologica*, vol. 158, 1979, pp. 72-79.

Stephen Rothenburger et al., "In Vitro Antimicrobial Evaluation of Coated VICRYL* Plus Antibacterial Suture (Coated Polyglactin 910 with Triclosan) Using Zone of Inhibition Assays," *Surgical Infections*, vol. 3, supplement, 2002, pp. S-79-S87.

Allan Ronald, "The Etiology of Urinary Tract Infection: Traditional and Emerging Pathogens," *Dis. Mon.*, vol. 49, 2003, pp. 71-82.

Alain Meyrier, Urinary Tract Infections, vol. II, Chapter 7 of *The Schrier Atlas of Diseases of the Kidney*, ed. Robert W. Schrier, 1999.

Donald P. Griffith et al., "Urease: The Primary Cause of Infection-Induced Kidney Stones," *Investigative Urology*, vol. 13(5), Mar. 1976, pp. 346-350.

D.J. Stickler et al., "Control of Encrustation and Blockage of Foley Catheters," *The Lancet*, vol. 361, Apr. 26, 2003, pp. 1435-1437.

Ciba Specialty Chemicals. Ciba® IRGASAN® DP 300, Ciba® IRGACARE® MP Antimicrobials. Toxicological and ecological data; Official registrations. Jan. 2003. 16 pages.

Ciba Specialty Chemicals. Ciba® IRGASAN® DP 300, Ciba®IRGACARE® MP Antimicrobial active ingredient for personal care products. 2001. 16 pages.

Swartz, R., et al., "Biofilm Formation on Peritoneal Catheters Does Not Require the Presence of Infection," *ASAIO Trans.*, vol. 37, No. 4, Oct.-Dec. 1991, pp. 626-634.

Richards, G.K., et al., "Comparative Rates of Antibiotic Action Against *Staphylococcus epidermidis* Biofilms," *ASAIO Trans.*, vol. 37, No. 3, Jul.-Sep. 1991, pp. M160-M162.

Stamm, Walter E., "Catheter-Associated Urinary Tract Infections: Epidemiology, Pathogenesis, and Prevention,"*American Journal of Medicine*, vol. 91, No. 3B, Sep. 1991, pp. 65S-71S.

Golomb, Gershon, et al., "Prevention of Bacterial Colonization on Polyurethane in vitro by Incorporated Antibacterial Agent," *Journal of Biomedical Materials Research*, vol. 25, No. 8, Aug. 1991, pp. 937-952.

Mulhall, Anne, "Biofilms and Urethral Catheter Infections," *Nursing Standard*, vol. 5, No. 18, Jan. 23-29, 1991, pp. 26-28.

Chang, Chung Che, et al., "Effect of *Staphylococcus epidermidis* on Adherence of *Pseudomonas aeruginosa* and *Proteus mirabilis* to Polymethyl Methacrylate (PMMA) and Gentamicin-Containing PMMA," *Journal of Orthopaedic Research*, vol. 9, No. 2, Mar. 1991, pp. 284-288.

Liedberv, H., et al., "*Pseudomonas aeruginosa*: Adherence to and Growth on Different Urinary Catheter Coatings," *International Urology and Nephrology*, vol. 22, No. 5, 1990, pp. 487-492.

Anwar, Hosmin, et al., "Testing the Susceptibility of Bacteria in Biofilms to Antibacterial Agents," *Antimicrobial Agents and Chemotherapy*, Vo. 34, No. 3, 1990, pp. 2043-2046.

Dunne, W. Michael Jr., "Effects of Subinhibitory Concentrations of Vancomycin or Cefamandole on Biofilm Production by Coagulase-Negative Staphylococci," *Antimicrobial Agents and Chemotherapy*, vol. 34, No. 3, Mar. 1990, pp. 390-393.

Doughterty, Steven H., et al., "Endogenous Factors Contributing to Prosthetic Device Infections," *Infectious Disease Clinics of North America*, vol. 3, No. 2, Jun. 1989, pp. 199-209.

Speer, Anthony G., et al., "Biliary Stent Blockage with Bacterial Biofilm," *Annals of Internal Medicine*, vol. 108, No. 4, Apr. 1998, pp. 546-553.

Liedberg, H., et al., "Silver Coating of Urinary Catheters Prevents Adherence and Growth of *Pseudomonas aeruginosa*," *Urological Research*, vol. 17, No. 6, 1989, pp. 357-358.

Ramsay, J.W.A., et al., "Biofilms, Bacteria, and Bladder Catheters: A Clinical Study," *British Journal of Urology*, vol. 64, No. 4, Oct. 1989, pp. 395-398.

Farber, Bruce F., et al., "The Use of Nonsteroidal Antiinflammatory Drugs to Prevent Adherence of *Staphylococcus epidermidis* to Medical Polymers," *Journal of Infectious Diseases*, vol. 166, No. 4, Oct. 1992, pp. 861-865.

Farber, Bruce F., et al., "*Staphylococcus epidermidis* Extracted Slime Inhibits the Antimicrobial Action of Glycpeptide Antibiotics," *Journal of Infectious Diseases*, Vo.,161, No. 1, Jan. 1990, pp. 37-40.

Donnenfeld, E.D., et al., "Biofilm and Bacterial Adherence Inhibition with Sodium Salicylate," *Investigative Ophthamology & Visual Science*, vol. 35, No. 4, 1994, p. 2164.

Farber, B.F., et al., "*Staphylococcus aureus* Extracted Polysaccharide Interferes with the Antimicrobial Action of Glycopeptide Antibiotics," *Clinical Research*, vol.38, No. 2, 1990, p. 428A.

Farber, B.F., et al., "Extracted *S. epidermidis* Slime Interferes with the Antimicrobial Action of Glycopeptide Antibiotics," *Clinical Research*, vol. 37, No. 2, 1990, p. 428A.

Farber, B.F., et al., "Unique Properties of *S. epidermidis* Extractable Polysaccharide Slime (SEEP)," Clinical Research, vol. 36, No. 3, 1988, p. 455A.

Teichberg, Saul, et al., "Salicylic Acid Decreases Extracellular Biofilm Production by *Staphylococcus epidermidis*: Electron Microscope Analysis," *Journal of Infectious Diseases*, vol. 167, No. 6, 1993, pp. 1501-1503.

Farber, Bruce F., et al., "A Novel Antibiofilm Technology for Contact Lens Solutions," Ophthalmology, vol. 102, No. 5, May 1995, pp. 831-836.

Roberts, E.L., et al., "The Role of Sodiuym Salicylate in the Prevention of the Adherence of Acanthamoeba Castellanii to Unworn Contact Lenses," *Investigative Ophthalmology & Visual Science*, vol. 35, No. 4, 1994, p. 2150.

Donnenfeld, Eric D., et al., "Controlled Evaluation of a Bandage Contact Lens and a Topical Nonsteroidal Antiinflammatory Drug in Treating Traumatic Corneal Abrasions," *Ophthalmology*, vol. 102, No. 6, Jun. 1995, pp. 979-984.

Costerton, J. William, et al., "Bacterial Biofilms in Nature and Disease," *Annual Review of Microbiology*, vol. 41, 1987, pp. 435-464.

Parsons, C. Lowell, et al., "Inhibition of Sodium Urate Crystal Adherence to Bladder Surface by Polysaccharide," Journal of Urology, vol. 134, No. 3, Sep. 1985, pp. 614-616.

Kingston, D., et al., "Self-disinfecting Plastics for Intravenous Catheters and Prosthetic Inserts," *Journal of Hygiene*, Cambridge, vol. 96, 1986, pp. 185-198.

Sherman, Stuart, et al., "Stent-induced Pancreatic Ductal and Parenchymal Changes: Correlation of Endoscopic Ultrasound with ERCP," *Gastrointestinal Endoscopy*, vol. 44, No. 3, 1996, pp. 276-282.

Bridge, R., Polymer Extrusion. Honors Project for Chemical Engineering at University of Connecticut [online], May 1997 [retrieved on Feb. 11, 2002]. Retrieved from the Internet: URL:http://engr.uconn.edu/cheg/polymer/c2561hnp.htm.

Harris, L., Injection Molding. Honors Project for Chemical Engineering at University of Connecticut [online], May 1997 [retrieved on Feb. 11, 2002]. Retrieved from the Internet: URL:http://engr.uconn.edu/cheg/polymer/injmold.htm>.

Langer, R. "Drug Delivery and Targeting," *Nature*, 392: pp. 5-9 (1998).

Gristina et al., A., "Bacterial Adherence and the Glycocalyx and Their Role in Musculoskeletal Infection," *Orthopedic Clinics of North America*, vol. 15, No. 3, Jul. 1984, pp. 517-535.

Ikeda, F. et al., "Formation of Biofilm by Slime Producing *Staphylococcus epidermis* and Bactericidal Activity of Cefazolin," *Kansenshogaku zasshi, Journal of the Japanese Association for Infectious Diseases*, vol. 65, No. 7, Jul. 1991, pp. 875-882.

\* cited by examiner

IMPLANTABLE OR INSERTABLE MEDICAL DEVICES FOR CONTROLLED DRUG DELIVERY

RELATED APPLICATION DATA

This patent application is a continuation-in-part of U.S. Ser. No. 10/209,476 filed Jul. 31, 2002 and entitled "CONTROLLED DRUG DELIVERY," the disclosure of which is incorporated by reference.

This patent application is also a continuation-in-part of U.S. Ser. No. 10/071,840 filed Feb. 8, 2002 now U.S. Pat. No. 6,887,270 and entitled "IMPLANTABLE OR INSERTABLE MEDICAL DEVICE RESISTANT TO MICROBIAL GROWTH AND BIOFILM FORMATION," the disclosure of which is incorporated by reference.

TECHNICAL FIELD

This invention generally relates to medical devices, and more particularly to implantable or insertable medical devices and methods for their manufacture.

BACKGROUND INFORMATION

Numerous medical devices have been developed for the delivery of therapeutic agents to the body. In accordance with some delivery strategies, a therapeutic agent is provided within a polymeric matrix that is associated with an implantable or insertable medical device. Once the medical device is placed at the desired location within a patient, the therapeutic agent is released from the polymeric matrix.

Various techniques, including thermoplastic processing techniques, have been used for the manufacture of medical devices for the delivery of therapeutic agents to the body. However, many therapeutic agents are unstable under the processing conditions associated with such techniques. Accordingly, there is a continuing need for processing techniques that do not result in substantial degradation of the therapeutic agents, particularly those having low stability.

Numerous medical devices have also been developed for implantation or insertion into patients, which do not necessarily contain a therapeutic agent. Unfortunately, many such medical devices are commonly associated with some degree of patient discomfort or pain after being positioned within the patient. As a specific example, EVA based ureteral stents are widely used to facilitate drainage in the upper urinary tract (e.g., from the kidney to the bladder), for example, following ureteroscopy, endourerotomies, and endopyelotomy for ureteral strictures, as well as in other instances where ureteral obstruction may occur. However, such stents are typically associated with pain and discomfort in the bladder and flank area after insertion. At present, one way by which pain and discomfort are minimized is to orally administer drugs to the patient. To date the most commonly prescribed oral drugs are opioid analgesia, which are controlled substances and have the potential for abuse by patients.

SUMMARY OF THE INVENTION

According to one aspect of the present invention, implantable or insertable medical devices are provided, which comprise: (a) a biocompatible polymer; and (b) at least one therapeutic agent selected from an anti-inflammatory agent, an analgesic agent, an anesthetic agent, and an antispasmodic agent. The medical devices are adapted for implantation or insertion at sites associated with pain or discomfort upon implantation or insertion.

In many embodiments, the therapeutic agent will be selected from at least one of (i) ketorolac and pharmaceutically acceptable salts thereof (e.g., ketorolac tromethamine) and (ii) 4-diethylamino-2-butynylphenylcyclohexylglycolate and pharmaceutically acceptable salts thereof (e.g., oxybutynin chloride).

The medical device may also contain one or more optional agents, including one or more radio-opacifying agents such as bismuth subcarbonate (e.g., to enhance visibility), and one or more antimicrobial agents such as triclosan (e.g., to reduce microbial buildup along the device).

The implantable or insertable medical devices of the present invention can be provided with a variety of release profiles. For instance, a cumulative therapeutic agent release selected from 5%, 10%, 15%, 20%, 25%, 30%, 40%, 50%, 60%, 70%, 80%, 90%, 95%, and 99%, relative to the total therapeutic agent in the device, can be obtained after implantation or insertion for a period selected from 1 day, 2 days, 4 days, 1 week, 2 weeks, 1 month, 2 months, 4 months, 1 year and 2 years.

A variety of biocompatible polymers can be used in the medical devices of the present invention. For example, biocompatible polymers can be selected from polyether block amides, thermoplastic polyurethanes, ethylene-vinyl acetates, and/or polyoctenamers, among others.

In accordance with many embodiments of the present invention, the medical devices will comprise one or more polymeric matrix regions comprising the following: (a) one or more biocompatible polymers, (b) one or more therapeutic agents, (c) one or more optional radio-opacifying agents, and/or (d) one or more optional antimicrobial agents.

For example, in one embodiment, the medical device comprises a polymeric matrix region comprising biocompatible polymer, therapeutic agent and radio-opacifying agent. In another embodiment, medical device comprises (a) a first polymeric matrix region comprising a first biocompatible polymer and a therapeutic agent, and (b) a second polymer matrix region comprising a second biocompatible polymer and a radio-opacifying agent; the first and second biocompatible polymers may be the same or different.

In addition to one or more matrix regions, the medical devices can include various other regions, for example, hydrogel layers and/or barrier layers.

Other aspects of the present invention are directed to uses for the implantable or insertable medical devices disclosed herein. In general, these uses comprise reducing the pain or discomfort accompanying the implantation or insertion of such devices. Further uses may comprise, for example, reducing microbial buildup along the device.

Still other aspects of the present invention concern methods for manufacturing the implantable or insertable medical devices disclosed herein.

According to various embodiments of the present invention, methods of manufacturing polymeric matrices are provided, which comprise: (a) providing a combination that comprises biocompatible polymer and therapeutic agent; and (b) forming a polymeric matrix from the combination.

In some embodiments, forming the polymeric matrix comprises a thermoplastic process, such as an extrusion process. In general, it is preferred for various processes of the present invention to be conducted under conditions such that substantial degradation of the therapeutic agent is avoided. For example, where thermoplastic techniques are utilized, it may be useful to process the matrix at a temperature that is (a)

above the softening temperature of the biocompatible polymer, (b) below the melting point of the therapeutic agent, and (c) sufficiently low to avoid substantial degradation of the therapeutic agent. It is also desirable to control shear in many embodiments to avoid substantial degradation of the therapeutic agent.

As a specific example, an extruded matrix comprising ethylene-vinyl acetate (EVA) copolymer, ketorolac tromethamine and bismuth subcarbonate can be formed under conditions of diminished temperature and shear, such that the degradation level of the ketorolac tromethamine is less than 2%.

In other embodiments of the invention, forming the polymeric matrix comprises a solution forming process, for example, a solution coating process.

One advantage of the present invention is that implantable or insertable medical devices can be provided, which are able to provide localized relief of pain and discomfort upon implantation or insertion.

Another advantage of the present invention is that thermally sensitive therapeutic agents can be processed using thermoplastic processing techniques, which heretofore would have resulted in unacceptable degradation of therapeutic agent.

These and other embodiments and advantages of the present invention will become immediately apparent to those of ordinary skill in the art upon review of the Detailed Description and claims to follow.

DETAILED DESCRIPTION OF THE INVENTION

Figure 1:
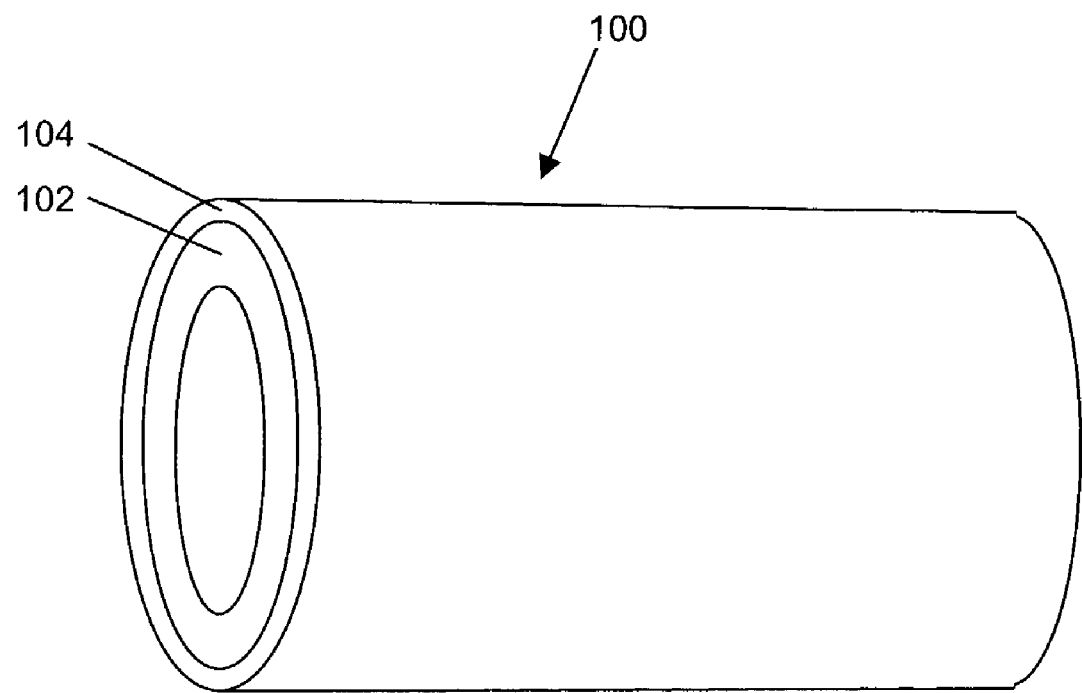
FIG. 1 is a simplified schematic representation of an annular medical device for implantation or insertion into the body, according to an embodiment of the invention.

In one aspect, the present invention is directed to an implantable or insertable medical device that comprises (a) a biocompatible polymer and (b) a therapeutic agent selected from an anti-inflammatory agent, an analgesic agent, a local anesthetic agent, and an antispasmodic agent. The medical device is of a type such that symptoms of pain or discomfort are typically experienced by the patient (e.g., a mammalian subject such as a human subject) after implantation or insertion.

Another aspect of the invention is directed to the use of such an implantable or insertable medical device to bring about a reduction in discomfort or pain subsequent to implantation or insertion (in addition to other therapeutic benefits that the device is implanted/inserted to provide, for example, to facilitate drainage, etc.). In some embodiments, the medical device will also be used to resist microbial growth and/or biofilm formation.

As a specific example, ureteral stents, for instance, ethylene-vinyl acetate (EVA) based ureteral stents, are widely used in urology to facilitate drainage in the upper urinary tract (e.g., from the kidney to the bladder) following various procedures (e.g., ureteroscopy, endourerotomies, endopyelotomy for ureteral strictures, as well as in other instances where ureteral obstruction is encountered). However, as noted above, such stents are typically associated with pain and discomfort after insertion. One way by which pain and discomfort are minimized is to orally administer drugs to the patient, which drugs are typically opioid analgesia having the potential for abuse by patients. In addition, drugs administered locally with the intention of providing a site-specific effect require significantly lower doses than oral administration of the same drug for the same therapeutic purpose. The advantage of the lower doses in site-specific delivery is that often unwanted or even toxic side affects of systemic concentrations of the same drug can be avoided.

A different approach is taken in various embodiments of the invention, wherein the pain and discomfort associated with the presence of implantable or insertable medical devices is addressed locally, rather than systemically. In these embodiments, a therapeutic agent selected from an anti-inflammatory agent, an analgesic agent, an anesthetic agent, and an antispasmodic agent is disposed within the medical device in a fashion such that the therapeutic agent is released into the patient upon implantation or insertion of the device. Medical devices having an extended release profile are preferred in many cases. By "extended release profile" is meant a release profile by which a therapeutically effective amount of therapeutic agent continues to be released for up to 1 day, 2 days, 4 days, 1 week, 2 weeks, 1 month, 2 months, 6 months, 1 year or even 2 years, in some embodiments after implantation/insertion.

The medical devices for use in connection with the present invention may be selected from essentially any implantable or insertable medical device. Examples of implantable medical devices include stents, stent grafts, stent covers, catheters, venous access devices, vena cava filters, peritoneal access devices, injectables/bulking agents, sutures, surgical meshes, enteral feeding devices used in percutaneous endoscopic gastronomy, prosthetic joints, and artificial ligaments and tendons.

Catheters for the practice of the present invention include urinary and vascular catheters.

Stents for the practice of the present invention include biliary, urethral, ureteral, tracheal, coronary, gastrointestinal, and esophageal stents. The stents may be of any shape or configuration. The stents may comprise a hollow tubular structure, which is particularly useful in providing flow or drainage through ureteral or biliary lumens. Stents may also be coiled or patterned as a braided or woven open network of fibers or filaments or, for example, as an interconnecting open network of articulable segments. Thus, stents can have a continuous wall structure or discontinuous open network wall structure.

Stent covers for the practice of the present invention may comprise a tubular or sheath-like structure adapted to be placed over a stent, which can comprise, for example, an open mesh of knitted, woven or braided design. The stent can be made of any material useful for such purpose including metallic and non-metallic materials as well as shape memory materials. Among useful metallic materials include, but are not limited to, shape memory alloys such as nickel-titanium alloys and other metallic materials including, but not limited to, stainless steel, tantalum, nickel-chrome, or cobalt-chromium, for example, Nitinol® and Elgiloy®.

In many embodiments of the invention, a therapeutic agent of interest is released from a polymeric matrix. The term "polymeric matrix" refers to a region that comprises a biocompatible polymer and at least one additive, for example, one or more therapeutic agents, one or more radio-opacifying agents, one or more pigments, and/or one or more antimicrobial agents, among other materials. The polymeric matrix can constitute the entirety of an implantable or insertable medical device, or it can correspond to only a portion or region of the medical device.

Where only a single distinct polymeric matrix region is provided in the medical device, the polymeric matrix region will preferably contain the therapeutic agent as well as any optional additives, such as radio-opacifying agents, pigments, antimicrobial agents, plasticizers, lubricants, and so forth. In other embodiments, the medical device comprises two or more distinct polymeric matrix regions. Where two or more distinct polymeric matrix regions are present in the medical device, it is not necessary that the therapeutic agent and any optional additive(s) be present in a single polymeric matrix region. For example, a therapeutic agent may be present in a first polymeric matrix region, and one or more optional additives may be present in a second polymeric matrix region distinct from the first polymeric matrix region.

Without wishing to be bound by theory, it is believed that therapeutic agent is released from a non-biodegradable polymeric matrix region, at least in part, by a mechanism wherein the polymeric matrix imbibes or contacts physiological fluid. In such a polymeric matrix, the therapeutic agent may diffuse to some extent through the polymer matrix toward an external surface and/or the physiological fluid diffuses into the polymeric matrix. The therapeutic agent then dissolves in the physiological fluid. A concentration gradient is believed to be set up at or near the matrix region, and the therapeutic agent in solution is then released via diffusion into the surrounding physiological fluid and local tissues. Where the polymeric matrix is biodegradable, similar diffusion-dissolution-diffusion processes may also occur. In a biodegradable polymeric matrix, however, therapeutic agent may also be released as the biodegradable polymeric matrix containing the therapeutic agent biodegrades upon contact with the physiological environment where the device is implanted/inserted. Thus, in a biodegradable polymer, therapeutic agent may be released by dissolution/diffusional processes and upon biodegradation of the polymer matrix.

In general, the therapeutic agent for use in connection with the present invention can be any pharmaceutically acceptable therapeutic agent. As used herein "pharmaceutically acceptable" means that an agent that is approved or capable of being approved by the United States Food and Drug Administration or Department of Agriculture for use in humans or animals when incorporated in or on an implantable or insertable medical device. As noted above, preferred therapeutic agents include anti-inflammatory agents, analgesic agents, local anesthetic agents, antispasmodic agents, and combinations thereof.

Anti-inflammatory agents include steroidal and non-steroidal anti-inflammatory agents. Examples of non-steroidal anti-inflammatory drugs include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid and its derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefienolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, paracaine, propipocaine, propoxycaine hydrochloride, pseudocaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenylpropylamine, tropenzile, trospium chloride, xenytropium bromide, and pharmaceutically acceptable salts thereof.

Two particularly preferred therapeutic agents for the practice of the present invention are (a) ketorolac and pharmaceutically acceptable salts thereof (e.g., the tromethamine salt thereof, sold under the commercial name Toradol®) and (b) 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropan®).

The amount of the therapeutic agent present in the polymeric matrix is an amount effective to reduce the pain or discomfort associated with the medical device. Typically, the therapeutic agent is present in a polymeric matrix in a range from about 0.1% to about 40% by weight of the polymeric matrix (including 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, and ranges between any two of these points, for instance, 0.1-10%, 10-20% and 20-30%, etc.). Where the oxybutynin chloride and ketorolac tromethamine are used, a range of 2-20% is typical, more typically 5-15%.

The amount of therapeutic agent present in a polymeric matrix will depend upon, inter alia, the efficacy of the therapeutic agent employed, the length of time during which the medical device is to remain implanted, as well as the rate at which the polymeric matrix or barrier layer releases the therapeutic agent in the environment of the implanted medical device. Thus, a device that is intended to remain implanted for a longer period will generally require a higher percentage of the therapeutic agent. Similarly, a polymeric matrix that provides faster rate of release of the therapeutic agent may require a higher percentage of the therapeutic agent. One skilled in the art can readily determine an appropriate therapeutic agent content to achieve the desired outcome.

The medical device of the present invention may also contain optional additives, including radio-opacifying agents, pigments, anti-microbial agents, and other additives such as plasticizers and extrusion lubricants, within its structure.

Thus, in some embodiments, the medical device further comprises a radio-opacifying agent, while in others it does not. For example, the radio-opacifying agent may be present in any polymeric matrix region or may be uniformly distributed throughout the medical device.

The radio-opacifying agent facilitates viewing of the medical device during insertion of the device and at any point while the device is implanted. A radio-opacifying agent typically functions by scattering x-rays. The areas of the medical device that scatter the x-rays are detectable on a radiograph. Among radio-opacifying agents useful in the medical device of the present invention are included a bismuth salt such as bismuth subcarbonate, bismuth oxychloride, bismuth trioxide, barium sulfate, tungsten, and mixtures thereof, with bismuth salts typically being preferred. Where present, the radio-opacifying agent is typically present in an amount of from about 10% to about 40% (including 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% and 40%, as well as ranges between any two of these values, e.g., 10-15%, 15-20%, 20-25%, 25-30%, 30-35%, 35-40%, and so forth, with 15-30% being more typical, even more typically 20-25%). One skilled in the art can readily determine an appropriate radio-opacifying agent content to achieve the desired visibility.

Where bismuth subcarbonate is used as a radio-opacifying agent, increasing the bismuth subcarbonate content can result in either a softer or a stiffer material, dependent upon base material to which the bismuth subcarbonate is added.

In some embodiments of the present invention, the medical device further comprises an antimicrobial agent, while in others it does not. The term "antimicrobial agent" as used herein means a substance that kills and/or inhibits the proliferation and/or growth of microbes, particularly bacteria, fungi and yeast. Antimicrobial agents, therefore, include biocidal agents and biostatic agents as well as agents that possess both biocidal and biostatic properties. In the context of the present invention, the antimicrobial agent kills and/or inhibits the proliferation and/or growth of microbes on and around the surfaces of an implanted medical device, and can therefore inhibit biofilm formation in some cases.

The antimicrobial agent can be any pharmaceutically acceptable antimicrobial agent. Preferred antimicrobial agents include triclosan, chlorhexidine, nitrofurazone, benzalkonium chlorides, silver salts and antibiotics such as rifampin, gentamycin and minocyclin and combinations thereof. The antimicrobial agent can be included in an amount ranging from 1-30 wt % (including 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and ranges between any two of these points, for instance, 1-5%, 5-10%, 10-15%, 15-20%, etc.). As a specific example, where triclosan is used as an antimicrobial agent, it is typically present in an amount ranging from 10-30%, more typically 5-15%.

Similar to the therapeutic agent, the amount of optional antimicrobial agent present in the structure will depend, inter alia, upon the efficacy of the agent employed, the length of time during which the medical device is intended to remain implanted, as well as the rate of release into the environment of the implanted medical device. Thus, a device that is intended to remain implanted for a longer period will generally require a higher percentage of the antimicrobial agent. Similarly, a faster release of the antimicrobial agent may require a higher amount of the bioactive agent. One skilled in the art can readily determine an appropriate antimicrobial agent content to achieve the desired outcome.

In this connection, it is noted that certain of the therapeutic agents listed above are useful in providing microbial resistance. For example, non-steroidal anti-inflammatory drugs (NSAIDs), for example, salicylic acid, its salts and its derivatives, have been described as microbial attachment/biofilm synthesis inhibitors. A "microbial attachment/biofilm synthesis inhibitor" is a substance that inhibits the attachment of microbes onto a surface and/or the ability of such microbes to synthesize or accumulate biofilm on a surface. Further information can be found in the above-incorporated U.S. Ser. No. 10/071,840.

In some embodiments, the medical device further comprises a pigment, while in others it does not. Pigments include any biocompatible and pharmaceutically acceptable colorant, regardless of type or color, including titanium dioxide, phthalocyanine organic pigments, quinaridone organic pigments, carbon black, iron oxides, and ultramarines. Where present, pigment is typically included in an amount ranging from 0.001 to 5%, more typically from 0.01 to 1%.

The polymeric regions used in the implantable or insertable medical device of the present invention may comprise any biocompatible polymer suitable for use in implantable or insertable medical devices. The biocompatible polymer may be substantially non-biodegradable or biodegradable.

The term "biocompatible" as used herein describes a material that is not substantially toxic to the human body, and that does not significantly induce inflammation or other adverse response in body tissues. Biocompatible polymers include essentially any polymer that is approved or capable of being approved by the United States Food and Drug Administration or Department of Agriculture for use in humans or animals when incorporated in or on an implantable or insertable medical device. Substantially non-biodegradable biocompatible polymers include thermoplastic and elastomeric polymeric materials. Polyolefins such as polyethylenes (e.g., metallocene catalyzed polyethylenes), polypropylenes, and polybutylenes, polyolefin copolymers, e.g., ethylenic copolymers such as ethylene vinyl acetate (EVA) copolymers, ethylene-methacrylic acid copolymers and ethylene-acrylic acid copolymers, where some of the acid groups can be neutralized with either zinc or sodium ions (commonly known as ionomers); vinyl aromatic polymers such as polystyrene; vinyl aromatic copolymers such as styrene-isobutylene copolymers and butadiene-styrene copolymers; polyacetals; chloropolymers such as polyvinyl chloride (PVC); fluoropolymers such as polytetrafluoroethylene (PTFE); polyesters such as polyethyleneterephthalate (PET); polyester-ethers; polyamides such as nylon 6 and nylon 6,6; polyethers; polyamide ethers such as polyether block amides (PEBA); polyoctenamers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Carbothane®, Tecoflex®, Tecothane®, Tecophilic®, Tecoplast®, Pellethane®, Chronothane® and Chronoflex®); silicones; polycarbonates; and mixtures and block, alternating, or random copolymers of any of the foregoing are non-limiting examples of non-biodegradable biocompatible polymers useful in the medical devices of the present invention.

Among particularly preferred non-biodegradable polymers are polyether block amides (PEBA), polyoctenamers such as Vestenamerg from Degussa Corp., Parsippany, N.J., which is a mixture of cyclic and linear polyoctenamers, polyolefins, ethylenic copolymers including ethylene vinyl acetate copolymers (EVA) and copolymers of ethylene with acrylic acid or methacrylic acid; thermoplastic polyurethanes (TPU) and polyurethane copolymers; metallocene catalyzed polyethylene (mPE), mPE copolymers, ionomers, and mixtures and copolymers thereof; and vinyl aromatic polymers and copolymers. Among preferred vinyl aromatic copolymers are included copolymers of polyisobutylene with polystyrene or polymethylstyrene, even more preferably polystyrene-polyisobutylene-polystyrene triblock copolymers.

These polymers are described, for example, in U.S. Pat. Nos. 5,741,331, 4,946,899 and U.S. Pat. Appln. No. 20020107330, each of which is hereby incorporated by reference in its entirety.

Ethylene vinyl acetate (EVA) is a particularly preferred non-biodegradable biocompatible polymer. Examples include EVA polymers having a vinyl acetate content of from about 5% to about 40% (including 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 35%, 36%, 37%, 38%, 39%, 40%, and including ranges between any two of these points, e.g., 5-10%, 10-15%, 15-20%, 20-25%, 25-30%, and so forth, with 10-30% being typical). Increasing the EVA content typically results in a softer material, while decreasing the EVA content typically produces a harder material.

Among preferred biodegradable polymers are included polylactic acid, polyglycolic acid and copolymers and mixtures thereof such as poly(L-lactide) (PLLA), poly(D,L-lactide) (PLA); polyglycolic acid [polyglycolide (PGA)], poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL), poly(glycolide-co-caprolactone) (PGA/PCL); polyethylene oxide (PEO), polydioxanone (PDS), polypropylene fumarate, poly(ethyl glutamate-co-glutamic acid), poly(tert-butyloxy-carbonylmethyl glutamate), poly(carbonate-ester)s, polycaprolactone (PCL), polycaprolactone co-butylacrylate, polyhydroxybutyrate (PHBT) and copolymers of polyhydroxybutyrate, poly(phosphazene), poly(phosphate ester), poly(amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], cyanoacrylate, polyethylene oxide, hydroxypropylmethylcellulose, polysaccharides such as hyaluronic acid, chitosan and regenerate cellulose, and proteins such as gelatin and collagen, and mixtures and copolymers thereof, among others.

The medical devices of the present invention may comprise a multilayer structure comprising two or more layers. For example, the medical devices can comprise one or more polymeric matrix regions as noted above. Furthermore, the medical devices may comprise a combination of two or more types of biocompatible polymers to produce desired physical properties for the medical devices. The medical devices can also comprise one or more barrier regions as well.

Multilayer structures of the present invention need not comprise a barrier layer. For example, a medical device in accordance with the present invention may comprise a two-layer structure comprising a first polymeric matrix layer containing biocompatible polymer, therapeutic agent and radio-opacifying agent, and a second layer on an external surface of the first polymeric matrix layer that provides lubricity. Such a lubricious layer may be desirable, for example, to facilitate insertion, implantation and/or removal of the medical device. A simplified schematic representation of a device of this type is depicted in FIG. 1, in accordance with an embodiment of the present invention. Implantable or insertable medical device 100 comprises an annular polymeric matrix region 102, which further comprises a biocompatible polymer (e.g., EVA), a therapeutic agent (e.g., ketorolac tromethamine or oxybutynin chloride) and a radio-opacifying agent (e.g., bismuth subcarbonate). The device 100 also comprises a lubricious layer 104 (e.g., a hydrogel layer) at least partially covering an exterior surface of the annular polymeric matrix region 102.

Figure 2:
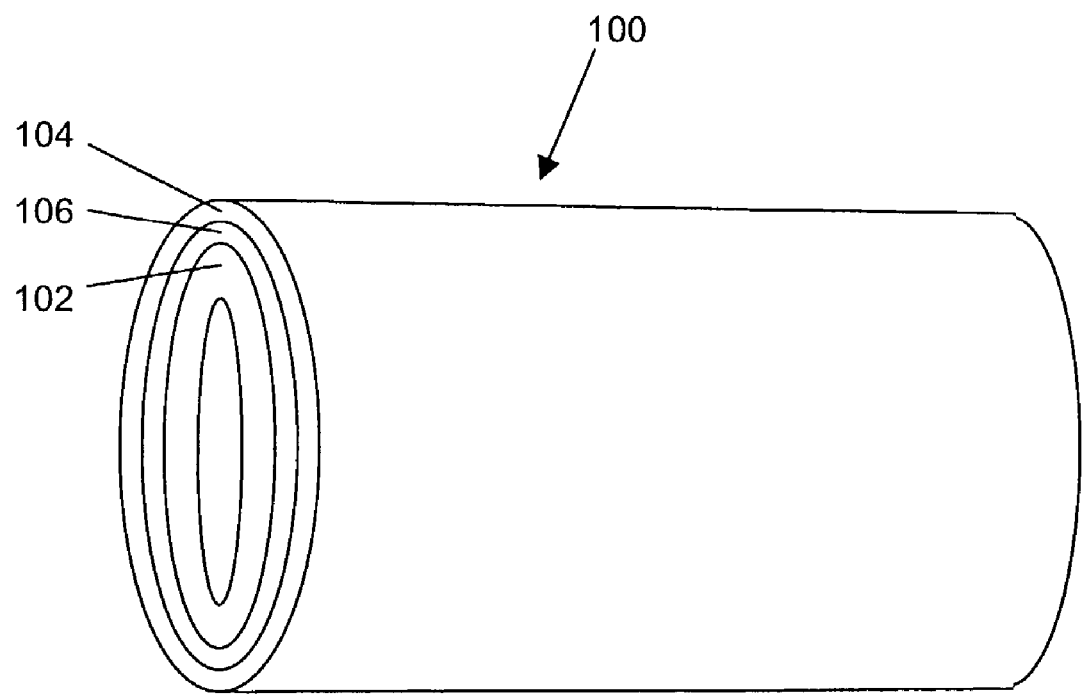
FIG. 2 is a simplified schematic representation of an annular medical device for implantation or insertion into the body, according to another embodiment of the invention.

As another example, a medical device in accordance with the present invention may comprise a three-layer structure comprising a first layer comprising biocompatible polymer, radio-opacifying agent and therapeutic agent, a second layer on an external surface of the first layer that acts as a barrier layer, and a third layer on an external surface of the second layer that provides lubricity. A simplified schematic representation of a device of this type is depicted in FIG. 2, in accordance with an embodiment of the present invention. Referring now to FIG. 2, implantable or insertable medical device 100 comprises an annular polymeric matrix region 102, which further comprises a biocompatible polymer (e.g., EVA), a therapeutic agent (e.g., ketorolac tromethamine or oxybutynin chloride) and a radio-opacifying agent (e.g., bismuth subcarbonate). The device 100 also comprises a polymeric barrier layer 106 (e.g., an EVA barrier layer) at least partially covering an exterior surface of the annular polymeric matrix region 102. The device 100 further comprises a lubricious layer 104 (e.g., a hydrogel layer) at least partially covering an exterior surface of the polymeric barrier layer 106.

Figure 3:
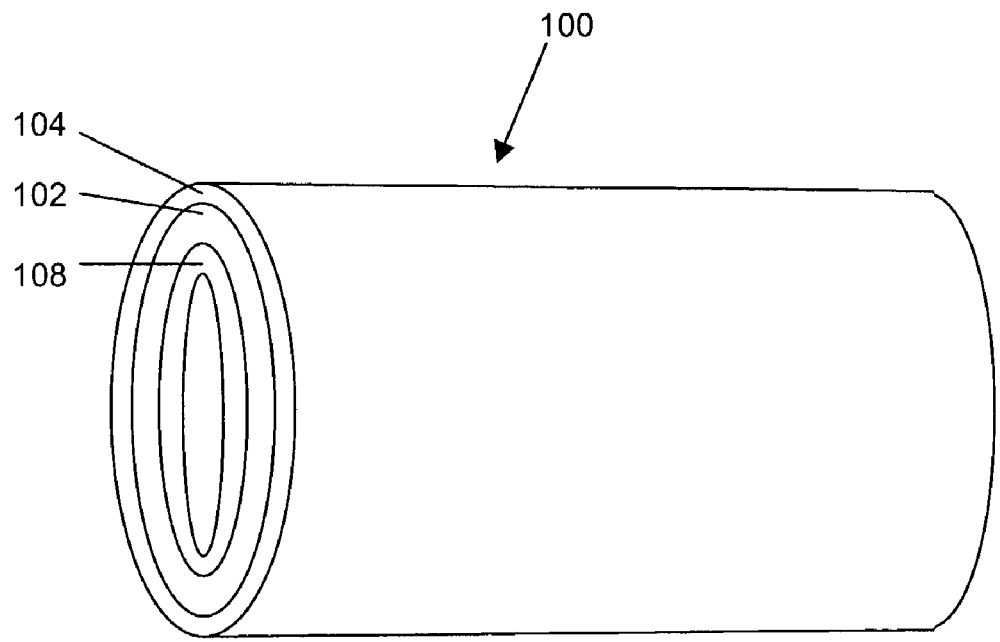
FIG. 3 is a simplified schematic representation of an annular medical device for implantation or insertion into the body, according to yet another embodiment of the invention.

As another example, a medical device in accordance with the present invention may comprise a three-layer structure comprising a first layer comprising biocompatible polymer and radio-opacifying agent, a second layer on an external surface of the first layer comprising biocompatible polymer and the therapeutic agent, and a third layer on an external surface of the second layer that provides lubricity. A simplified schematic representation of a device of this type is depicted in FIG. 3, in accordance with an embodiment of the present invention. Referring now to FIG. 3, implantable or insertable medical device 100 comprises an annular radio-opaque region 108, which comprises a biocompatible polymer (e.g., EVA) and a radio-opacifying agent (e.g., bismuth subcarbonate). Over the radio-opaque region 108 lies an annular polymeric matrix region 102, which further comprises a biocompatible polymer (e.g., EVA) and a therapeutic agent (e.g., ketorolac tromethamine or oxybutynin chloride). The device 100 also comprises a lubricious layer 104 (e.g., a hydrogel layer) at least partially covering an exterior surface of the annular polymeric matrix region 102.

Figure 4:
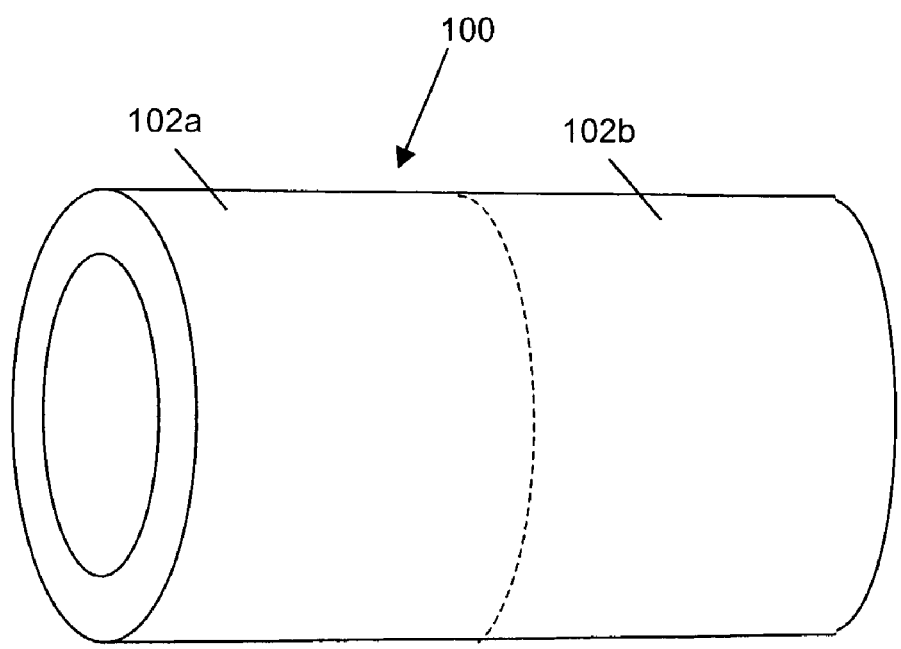
FIG. 4 is a simplified schematic representation of an annular medical device for implantation or insertion into the body, according to yet another embodiment of the invention.

As another example, a medical device in accordance with the present invention may comprise a structure comprising (a) a first region comprising a first therapeutic agent and a first biocompatible polymer, and (b) a second region comprising a second therapeutic agent and a second biocompatible polymer. The regions may differ, for example, (a) because the first therapeutic agent differs from the second therapeutic agent, (b) because the first biocompatible polymer differs from the second biocompatible, or (c) because the first therapeutic agent differs from the second therapeutic agent and because the first biocompatible polymer differs from the second biocompatible polymer. A simplified schematic representation of a device of this type is depicted in FIG. 4, in accordance with an embodiment of the present invention. Referring now to FIG. 4, implantable or insertable medical device 100 comprises a first annular polymeric matrix section 102a, which comprises a relatively soft matrix region, a therapeutic agent, and a radio-opacifying agent. The medical device 100 further comprises a second annular polymeric matrix section 102b, which comprises a relatively hard matrix region, a therapeutic agent, and a radio-opacifying agent. A medical device of this type may be formed using a variety of extrusion techniques, including, for example, interrupted layer co-extrusion (ILC). See, for example, extrusion processes described in U.S. Pat.

Nos. 5,622,665 and 6,508,805, which are hereby incorporated by reference. By virtue of the LC process, the relatively soft (low durometer) polymer section 102a will transition to the relatively hard (high durometer) polymer section 102b. The transition between these regions is schematically illustrated by a dashed line in FIG. 4.

It should be clear from the above that myriad possibilities exist regarding the regions that can comprise the medical devices of the present invention, for example, the type of regions (e.g., matrix regions, barrier regions, lubricious regions, etc.), the number of these regions, the shape of these regions, the distribution of these regions within the device, the composition of these regions, and so forth. As specific examples, (a) multiple regions (e.g., layers, sections, etc.) can be provided in one portion of the device, but not another, (b) different polymers can be provided in different regions of the device (e.g., different polymers in different layers along the radius of the device, or different polymers in different sections along the length of the stent), (c) different therapeutic agents can be provided in different regions of the device (e.g., different therapeutic agents in different layers along the radius of the device, or different therapeutic agents in different sections along the length of the stent), (d) different therapeutic agent concentrations can be provided in different regions of the device (e.g., different therapeutic agent concentrations in along the radius of the device, or different therapeutic agent concentrations along the length of the stent), and so forth.

Medical devices in accordance with the present invention having multiple layer structures may provide certain advantages relative to single layer devices. For example, a barrier layer can be provided to control the rate of release of therapeutic agent from an adjacent layer. It is understood, however, that the medical device of the present invention is not limited to a multiple region structure and, indeed, a single region structure, for example, an annular tube comprising biocompatible polymer, therapeutic agent, and optional radio-opacifying agent is within the scope of the present invention.

The release characteristics of a particular therapeutic agent (or a particular optional antimicrobial agent) commonly depend on the ability of the therapeutic agent (or optional antimicrobial agent) to diffuse from a particular polymeric matrix. Polymer matrices of different compositions typically exhibit different release characteristic. In this connection, release characteristics may be changed by changing, for example, (1) the amount and type of biocompatible polymer, (2) the amount and type of therapeutic agent (or optional antimicrobial agent), and (3) the amount and type of any additional additives including radio-opacifying agents, pigments, and so forth. Some compositions may result in relatively fast release while others may result in a slower release profile. By appropriate selection of the materials comprising the polymeric matrix, as well as their respective amounts, the release profile of the therapeutic agent (or optional antimicrobial agent) from the device may be optimized for a particular application.

Where used, lubricious layers preferably comprise one or more hydrogels. Hydrogels are typically hydrophilic polymeric materials that have the ability to absorb large amounts, up to many times the weight of the hydrogel itself, of water or other polar molecules. Hydrogels have been disclosed as coatings for implantable or insertable medical devices or as materials for constructing the device itself in, for example, U.S. Pat. Nos. 6,316,522; 6,261,630; 6,184,266; 6,176,849; 6,096,108; 6,060,534; 5,702,754; 5,693,034; and, 5,304,121, each of which is incorporated by reference and assigned to Boston Scientific Corporation or SciMed Life Systems, Inc.

Hydrogels can be based on synthetic or naturally occurring materials or a composite thereof; can be biodegradable or substantially non-biodegradable; and, can be modified or derivatized in numerous ways to render the hydrogel more suitable for a desired purpose. For example, a hydrogel can be modified by chemically cross-linking with, for example, a polyfunctional cross-linking agent that is reactive with functional groups covalently bonded to the polymer structure. A hydrogel can also be ionically cross-linked with, for example, polyvalent metal ions. Hydrogels can also be both chemically and ionically cross-linked. Examples of hydrogel polymers include polyacrylates; poly(acrylic acids); poly(methacrylic acids); polyacrylamides; poly(N-alkylacrylamides); polyalkylene oxides; poly(ethylene oxide); poly(propylene) oxide; poly(vinyl alcohol); polyvinyl aromatics; poly(vinylpyrrolidone); poly(ethyleneimine); polyethylene amine; polyacrylonitrile; polyvinyl sulfonic acid; polyamides; poly (L-lysine); hydrophilic polyurethanes; maleic anhydride polymers; proteins; collagen; cellulosic polymers; methyl cellulose; carboxymethyl cellulose; dextran; carboxymethyl dextran; modified dextran; alginates; alginic acid; pectinic acid; hyaluronic acid; chitin; pullulan; gelatin; gellan; xanthan; carboxymethyl starch; chondroitin sulfate; guar; starch; and copolymers, mixtures and derivatives thereof. Suitable hydrophilic coatings include polyacrylic acid polymers available, for example, from Boston Scientific Corp., Natick, Mass., under the trade designation HydroPlus™ and described in U.S. Pat. No. 5,091,205, the disclosure of which is hereby incorporated herein by reference. Another suitable hydrogel is HydroPass™ also available from Boston Scientific Corp., Natick, Mass.

Where used, barrier layers preferably comprise polymeric materials. Any of the non-biodegradable and biodegradable polymers described hereinabove in relation to the polymeric matrix may also form a barrier layer. Preferred barrier layer polymers include EVA, PEBA, TPU, polyoctenamers and mixtures thereof.

A barrier layer and any underlying polymeric matrix region may comprise the same or different polymeric materials. Different polymeric materials will generally provide different rates of diffusion or release of therapeutic agent. Thus, less permeable barrier layers may be provided to control the rate of release of a therapeutic agent from an underlying polymeric matrix region, which may be more permeable to diffusion of a therapeutic agent. For example, where an EVA copolymer is used as the polymeric matrix, another EVA copolymer having a higher vinyl acetate content may be useful to form the barrier layer. Higher vinyl acetate content EVA copolymers are useful as barrier layers due to their lower permeability to certain therapeutic agents, and hence their ability to release therapeutic agent more slowly than lower vinyl acetate content copolymers. The relative rigidity or stiffness of such higher vinyl acetate content barrier layers may be offset somewhat by the use of lower vinyl acetate content in the underlying polymeric matrix region, by the addition of additives that may increase softness, such as bismuth subcarbonate, to the underlying polymeric matrix region, and so forth.

Further, where a barrier (or other) layer is provided any of the above supplemental additives, for example radio-opacifying agent, anti-microbial agent, pigment, etc. may be provided in a barrier or other layer.

Thus, a medical device in accordance with the present invention, for example, can be constructed of single/multiple layers/regions, can have one or multiple polymeric matrix regions, can have none, one or multiple barrier regions, and can have none, one or more lubricious regions, or other regions. Moreover, neither the polymeric matrix nor the barrier region nor the lubricous region need be annular as depicted in the Figures.

In accordance with another aspect of the present invention, methods of manufacturing an implantable or insertable medical device are provided, which comprise: (a) providing one or more biocompatible polymers, one or more therapeutic agents and, optionally, one or more radio-opacifying agents and/or anti-microbial agents; (b) forming at least a portion of the medical device by processing the one or more biocompatible polymer(s), therapeutic agent(s), and optional materials.

In this connection, it is noted that many therapeutic agents, including oxybutynin chloride and ketorolac tromethamine discussed above, are prone to substantial degradation under conditions of elevated temperature and/or mechanical shear. By "substantial degradation" is meant that more than 10% by weight of the therapeutic agent (based on the initial weight of the therapeutic agent) is degraded during processing. Accordingly, various embodiments of the present invention are directed to processing conditions that avoid substantial degradation of therapeutic agent. Preferably, less than 7%, 5%, 3%, or 2%, and more preferably less than 1% of any therapeutic agent is degraded during processing in accordance with the present invention.

Various techniques are available for forming at least a portion of a medical device from the biocompatible polymer(s), therapeutic agent(s), and optional materials, including solution processing techniques and thermoplastic processing techniques.

Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Preferred solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up a release region to a desired thickness.

In many embodiments, a solution containing solvent and biocompatible polymer is applied to a medical device substrate, or to another template such as a mold, to form a device or device portion of interest. In this way, polymeric regions, including barrier layers, lubricious layers, and so forth can be formed. If desired, the solution can further comprise, one or more of the following: therapeutic agent(s) and other optional additives such as radio-opacifying agent(s), pigment(s), anti-microbial agent(s), etc. in dissolved or dispersed form. This results in a polymeric matrix region containing these species after solvent removal.

In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the devices or device portions of the present invention include molding techniques (for example, injection molding, rotational molding, and so forth), extrusion techniques (for example, extrusion, co-extrusion, multi-layer extrusion, multi-lumen extrusion, and so forth) and casting.

Thermoplastic processing in accordance with the present invention typically comprises mixing or compounding, in one or more stages, the biocompatible polymer(s) and one or more of the following: therapeutic agent(s), radio-opacifying agent(s), pigment(s), anti-microbial agent(s), and so forth. The resulting mixture is then shaped into an implantable or insertable medical device or a portion thereof. The mixing and shaping operations, as described more fully below, may be performed using any of the conventional devices known in the art for such purposes. In the description, therapeutic agent(s), radio-opacifying agent(s), anti-microbial agent(s), pigment(s), and so forth will, at times, be referred to as "additives" or "agents."

During thermoplastic processing, there exists the potential for the therapeutic agent(s) to degrade, for example, due to elevated temperatures and/or mechanical shear that are associated with such processing. For example, oxybutynin chloride and ketorolac tromethamine, two therapeutic agents that are particularly preferred for the practice of the present invention, are prone to substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10%. More typically degradation is held to less than 7%, 5%, 3%, 2%, or preferably less than 1%. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in a preferred embodiment, biocompatible polymer is precompounded with radio-opacifying agent under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the medical device or device component of interest.

Conversely, in another embodiments, biocompatible polymer can be precompounded with therapeutic agent under conditions of reduced temperature and mechanical shear. This precompounded material is then mixed with radio-opacifying agent, also under conditions of reduced temperature and mechanical shear, and the resulting mixture is shaped into the medical device or device component of interest.

It has been noted by the inventors, that the presence of certain additives, for example, radio-opacifying agents such as bismuth subcarbonate, during thermoplastic processing results in substantially higher degradation of therapeutic agent than would otherwise occur under conditions of similar mechanical shear and temperature in the absence of these additives. Without wishing to be bound by theory, it is believed that the presence of these additives, which remain in solid form under typical thermoplastic processing conditions, create localized regions of heightened shear and/or temperature, increasing therapeutic agent degradation. However, when such additives are precompounded with the biocompatible polymer prior to addition of the therapeutic agent, or when therapeutic agent is precompounded with the biocompatible polymer prior to addition of such additives, the level of degradation can be substantially decreased. Once the therapeutic agent is added, further thermoplastic processing is typically conducted under temperature and mechanical shear conditions, which are as low as possible.

The conditions used to achieve a mixture of the biocompatible polymer and additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a polymeric matrix region is formed comprising EVA polymer, a radio-opacifying agent (e.g., bismuth subcarbonate), and a therapeutic agent prone to degradation by heat and/or mechanical shear (e.g., ketorolac tromethamine and/or oxybutynin chloride), it is preferred to premix the EVA with the radio-opacifying agent at temperatures of about 170-180° C., which are common processing conditions for EVA polymers. A twin screw extruder is preferred for this purpose, but other apparatus can be used. The therapeutic agent is then combined with the premixed composition and subjected to further thermoplastic processing at conditions of temperature and mechanical shear that are substantially lower than is typical for EVA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of ketorolac tromethamine and oxybutynin chloride, because processing at or above these temperatures will result in substantial therapeutic agent degradation. It is further noted that in certain embodiments, the processing temperature will be below the melting point of all bioactive compounds within the composition, including the therapeutic agent and any antibacterial agent that is present. After compounding, the resulting product is shaped into the desired form, also under conditions of reduced temperature and shear. For example, a single screw extruder can be used for this purpose, operated at substantially reduced temperatures (e.g., 105-110° C.) using substantially reduced volumetric output (e.g., less than 40% of full capacity, which generally corresponds to a volumetric output of less than 100 cc/min).

It is noted that some combinations of biocompatible polymer(s) and additive(s) can be processed at temperatures that are lower than otherwise might be expected. For example, 100-110° C. is a relatively low temperature for processing an EVA copolymer, a radio-opacifying agent such as bismuth subcarbonate, and a therapeutic agent such as ketorolac tromethamine or oxybutynin chloride. However, by adding an antimicrobial agent such as triclosan, which melts at a temperature of around 55° C., the triclosan can act as a plasticizer for the EVA, facilitating use of lower temperatures, for example, about 80° C. to about 90° C.

In other embodiments, biodegradable polymer(s) and one or more additives are premixed using non-thermoplastic techniques. For example, the biocompatible polymer can be dissolved in a solvent system containing one or more solvent species. Any desired agents (for example, radio-opacifying agent, therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, therapeutic agent can be dissolved or dispersed in a solvent system, which is then applied to a pre-existing polymeric region (the pre-existing polymeric region can be formed using a variety of techniques including solution and thermoplastic processing techniques, and it can comprise a variety of additives including radio-opacifying agent and/or pigment), whereupon the therapeutic agent is imbibed into the polymeric region. As above, the resulting solid material can then be granulated for further processing, if desired.

Extrusion processes are a preferred group of thermoplastic processes for the practice of the present invention. For example, as indicated above, a medical device or device portion can be formed by extruding a single annular polymeric matrix containing biocompatible polymer(s), therapeutic agent(s) and radio-opacifying agent(s).

Co-extrusion is a shaping process that can be used to produce a multi-region structure (for example, a structure comprising one or more polymeric matrix regions, and one or more barrier layers, each at least partially covering a surface of a polymeric matrix region). Multi-region structures can also be formed by other processing and shaping techniques such as co-injection or sequential injection molding technology.

Where multiple regions are provided, various processes, including any of those discussed above, can also be used in various combinations. For example, a barrier layer can be extruded onto a preformed polymeric matrix region using an extrusion coating process. This process is distinguished from a co-extrusion process in which the polymeric matrix and barrier layers are shaped substantially simultaneously. As another example, a barrier layer can be applied to a surface of a preformed polymeric matrix by applying a solution or dispersion of a barrier polymer onto a surface of a preformed polymeric matrix region followed by removing the solvent or liquid dispersing agent, e.g., by evaporation. Such a solution or dispersion of the barrier polymer may be applied by contacting a surface of the preformed polymeric matrix using any of the techniques discussed above, for example, dipping or spraying. Of course, the use of these additional shaping processes is not limited to the application of a barrier layer to a polymeric matrix region. For example, an additional polymeric matrix region or a lubricious coating may also be formed by similar methods, among other regions.

In many embodiments of the present invention, including various extrusion embodiments, the product that emerges from the thermoplastic processing device (e.g., an annulus, or tube, that emerges from an extruder) is cooled. Examples of cooling processes include air cooling and/or immersion in a cooling bath. In some preferred embodiments, a water bath is used to cool the extruded product. However, where a water-soluble therapeutic agent such as ketorolac tromethamine or oxybutynin chloride is used, the immersion time should be held to a minimum to avoid unnecessary loss of therapeutic agent into the bath. Immediate removal of water or moisture by use of ambient or warm air jets after exiting the bath will also prevent re-crystallization of the drug on the device surface, thus controlling or minimizing a high drug dose dump upon implantation or insertion.

Once a medical device is formed, it is typically packaged and sterilized. Implantable or insertable medical devices are commonly sterilized by exposure to ethylene oxide or to radiation. As in device formation, care should be taken during device sterilization to avoid unnecessary degradation of the therapeutic agent and prolonged exposure to moisture.

For example, where the medical device contains ketorolac tromethamine, ethylene oxide sterilization has been found to be less desirable, because this process involves exposing the therapeutic agent to heat, moisture and reactive chemicals. On the other hand, it is also noted that radiation sterilization can lead to degradation of the therapeutic agent. However, degradation can nonetheless be held to acceptable levels, for example, (a) by using a relatively low energy radiation, for instance, electron beam radiation, and (b) by minimizing exposure of the medical device to moisture, oxygen and light.

In one preferred embodiment, the medical device is placed in a foil pouch, which is either evacuated or is provided with an inert atmosphere (e.g., an atmosphere of nitrogen and/or noble gases such as argon, etc.), and the pouch is subsequently exposed to electron beam radiation.

The invention will be further described with reference to the following non-limiting Example. It will be apparent to those skilled in the art that many changes can be made in the embodiments described in such Example, consistent with the foregoing description, without departing from the scope of the present invention.

EXAMPLE

A single-layer matrix polymer structure is formed from a mixture containing 65.75 wt % and 52.75 wt % respectively of Elvax® 460, an ethylene vinyl acetate copolymer having a 18 wt % vinyl acetate content available from DuPont, (b) 26 wt % of bismuth subcarbonate as a radio-opacifying agent, (c) 8 wt % and 21 wt %, respectively, of ketorolac tromethamine, available from Spectrum Chemicals & Laboratory Products, as a non-steroidal anti-inflammatory drug, and (d) 0.25% blue pigment.

The bismuth subcarbonate, EVA copolymer, and blue color are precompounded at 350° (177° C.), for example, in a Haake twin screw extruder.

Ketorolac is then mixed with the pre-compounded resin, and the resulting mixture is compounded at 215° F. (102° C.) using a Haake twin screw extruder at a reduced shear rate (<30% of full screw power). About 6-8 inches of the length of extruded rod (instead of 6-8 feet of extruded length, which is more typical) is guided through a chilled water bath, followed by air drying. The total amount of degradation product in the compounded resin is less than 0.3% (w/w, against the total amount of drug loaded).

The compounded resin is then extruded into 6 Fr. tubes using a Davis Standard 1" single screw extruder at 225° F. Shear rate is controlled by keeping the screw rate under 16 rpm. The take-off rate is about 18 feet/min. As above, the extruded tube is subjected to a brief water cooling step, followed by air cooling. The total amount of degradation caused by this extrusion step is less than or equal to 0.2%.

A flow through model is used to simulate human body conditions to determine the release profile of ketorolac tromethamine. 50 cm length tubular samples of the above, which contain 8% and 21% ketorolac tromethamine, respectively, were loaded into the model. The following conditions were used: (a) release medium: artificial urine (normal pH ~6.5), which contains the components listed in Table 1 below, (b) flow rate: 0.50 mL/min, (c) temperature: 37° C., and (d) sample size: N=3.

Figure 5:
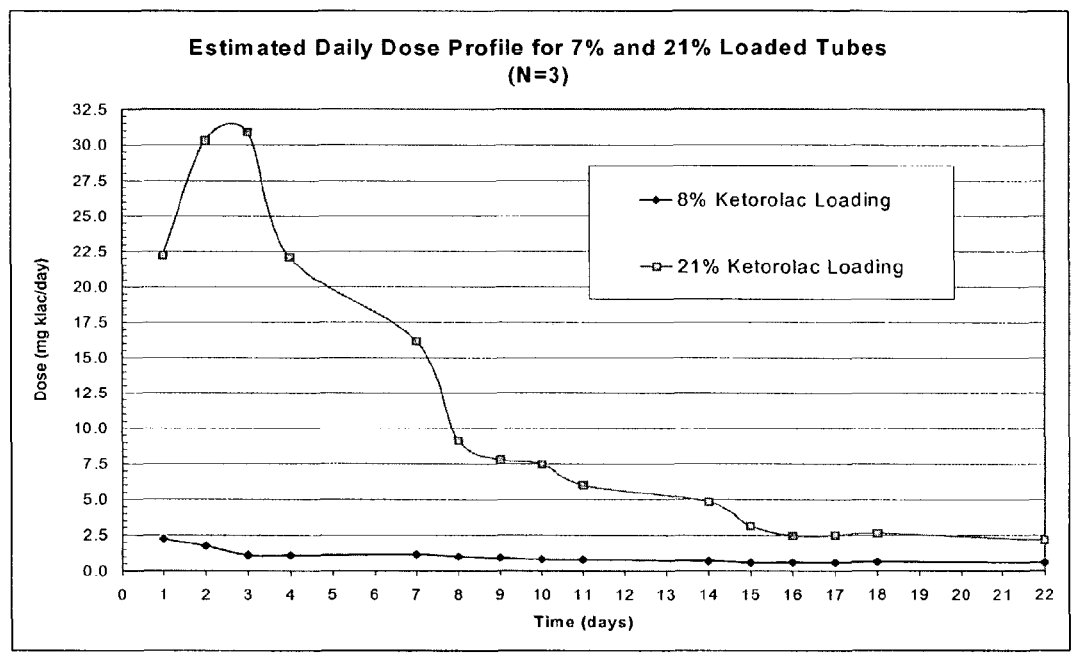
FIG. 5 is a plot of estimated daily dose of ketorolac based on release as a function of time at 37° C. in artificial urine, in accordance with an embodiment of the present invention.
Figure 6:
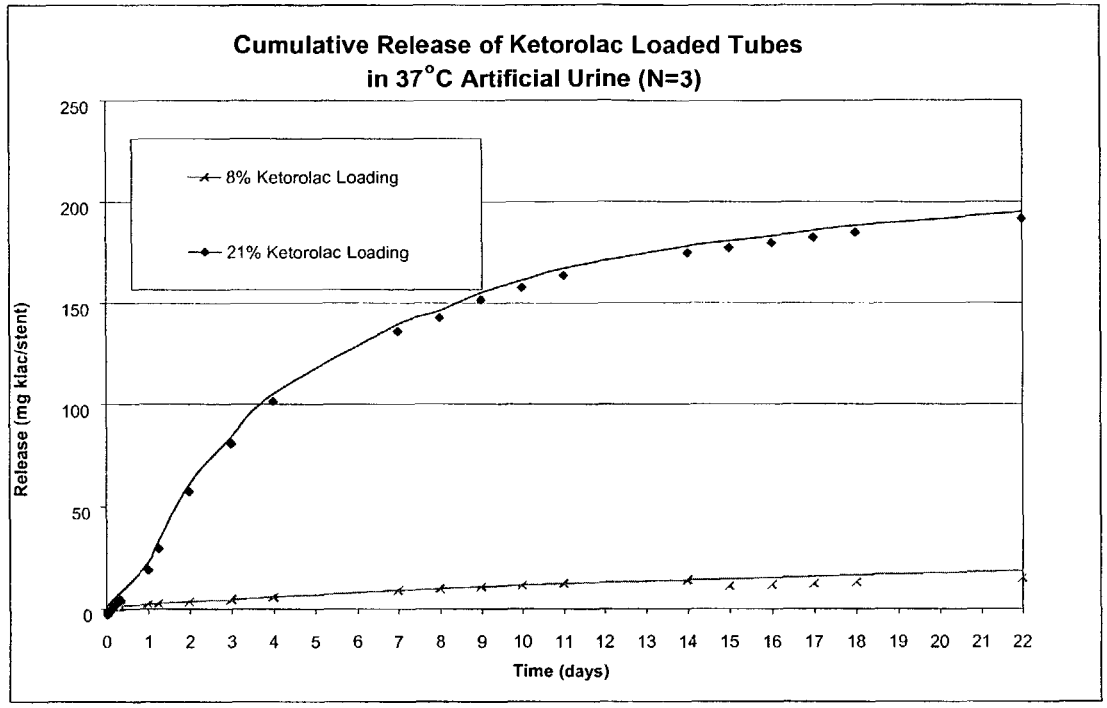
FIG. 6 is a plot of estimated in vitro cumulative ketorolac release based on release as a function of time at 37° C. in artificial urine, in accordance with an embodiment of the present invention.
Figure 7:
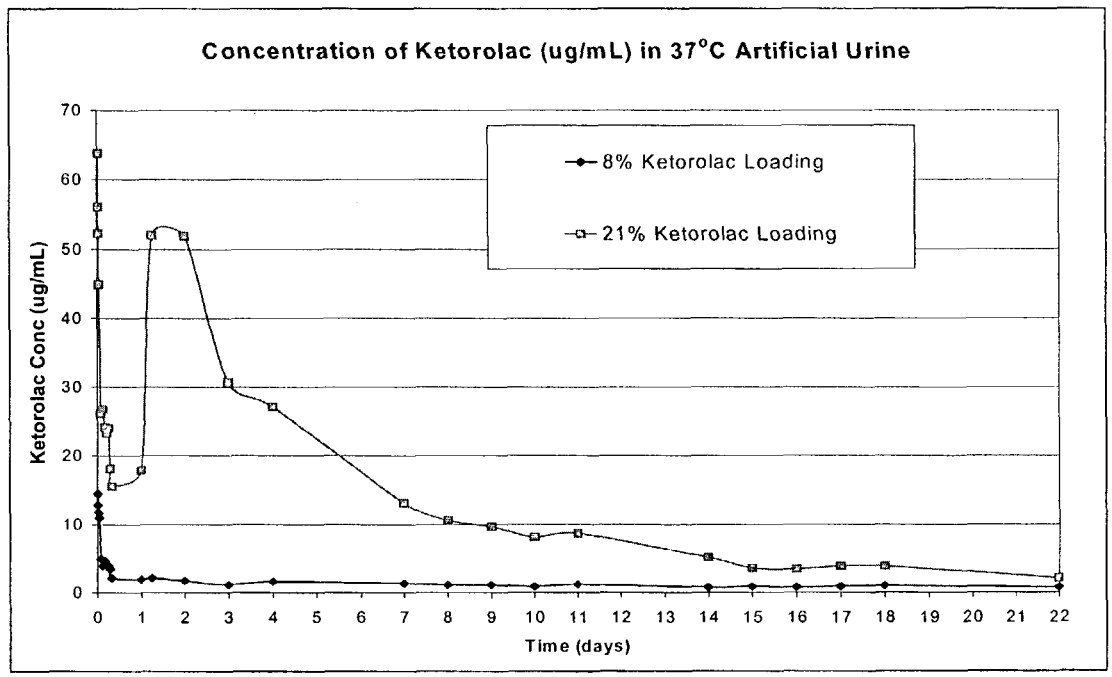
FIG. 7 is a plot of ketorolac concentration as a function of time at 37° C. in artificial urine, in accordance with an embodiment of the present invention.

Fluid samples are collected throughout the study and measured using HPLC to determine concentration of the therapeutic agent. The results are illustrated in FIGS. 5, 6 and 7, which present daily dose, cumulative release, and concentration, respectively, as a function of time.

TABLE 1

| Component | Grams | Wt % | Molarity | | Molarity | mmol/L | mg/dL |
|---|---|---|---|---|---|---|---|
| Urea | 19.4 | 1.94 | 3.33E−01 | Urea | 3.33E−01 | 333.3 | 2000 |
| NaCl | 8 | 0.80 | 1.41E−01 | Na | 1.77E−01 | 176.8 | 406.6 |
| MgSO$_4$*7H$_2$O | 1.1 | 0.11 | 4.61E−03 | Cl | 1.45E−01 | 145.1 | 522.5 |
| Na$_2$SO4 | 1.5 | 0.15 | 1.09E−02 | SO4 | 1.55E−02 | 15.5 | 148.9 |
| KH$_2$PO4 | 0.91 | 0.09 | 6.85E−03 | PO4 | 1.37E−02 | 13.7 | 130.0 |
| Na$_2$HPO4 | 0.94 | 0.09 | 6.83E−03 | Ca | 1.90E−03 | 1.9 | 7.6 |
| CaCl$_2$*2H$_2$O | 0.27 | 0.03 | 1.90E−03 | Mg | 4.61E−03 | 4.6 | 11.2 |
| DI Water | 969.25 | 96.79 | 5.56E+01 | K | 6.85E−03 | 6.9 | 26.7 |

Further aspects and embodiments of the invention will now be described. In one aspect, an implantable or insertable medical device is provided which comprises: (a) a biocompatible polymer; and (b) at least one therapeutic agent selected from an anti-inflammatory agent, an analgesic agent, an anesthetic agent, and an antispasmodic agent, wherein the medical device is adapted for implantation or insertion at a site associated with pain or discomfort upon implantation or insertion.

In certain embodiments, the medical device does not contain an antimicrobial agent.

In certain embodiments, the medical device further comprises a radio-opacifying agent.

In certain embodiments, the medical device is a ureteral stent.

Another aspect of the invention provides for the use of an implantable or insertable medical device. The use comprises reducing pain or discomfort accompanying implantation or insertion of the implantable or insertable medical device, which comprises, (a) a biocompatible polymer; and (b) at lease one therapeutic agent selected from an anti-inflammatory agent, an analgesic agent, an anesthetic agent, and an antispasmodic agent, and a radio-opacifying agent.

In certain embodiments, the implantable or insertable medical device further comprises a radio-opacifying agent.

In certain embodiments, the medical device is a ureteral stent.

In certain embodiments, the use of the device further comprises reducing microbial buildup along the device, wherein the device further comprises an antimicrobial agent.

In accordance with another aspect, an implantable or insertable medical device is provided that comprises: (a) a biocompatible polymer; and (b) at least one therapeutic agent selected from (i) ketorolac and pharmaceutically acceptable salts thereof and (ii) 4-diethylamino-2-butynylphenylcyclohexylglycolate and pharmaceutically acceptable salts thereof, wherein the medical device is adapted for implantation or insertion at a site that is associated with pain or discomfort upon implantation or insertion.

In certain embodiments, the therapeutic agent is ketorolac tromethamine.

In certain embodiments, the therapeutic agent is oxybutynin chloride.

In certain embodiments, the cumulative release of therapeutic agent is in an amount selected from 5%, 10%, 15%, 20%, 25%, 30%, 40%, 50%, 60%, 70%, 80%, 90%, 95%, and 99%, relative to the total therapeutic agent in the device, after implantation or insertion at the site for a period selected from 1 day, 2 days, 4 days, 1 week, 2 weeks, 1 month 2 months, 4 months, 1 year and 2 years.

In certain embodiments, the medical device is a ureteral scent.

In certain embodiments, the biocompatible polymer is selected from or more of polyether block amides (PEBA), thermoplastic polyurethanes (TPU), and polyoctenamers.

In certain embodiments, the biocompatible polymer is an ethylene-vinyl acetate (EVA) copolymer.

In certain embodiments, the medical device comprises a polymeric matrix region comprising the biocompatible polymer and the therapeutic agent.

In certain embodiments, the medical device further comprises a radio-opacifying agent.

In certain embodiments, the medical device comprises a polymeric matrix region comprising a biocompatible polymer, a therapeutic agent and a radio-opacifying agent.

In certain embodiments, the radio-opacifying agent is bismuth subcarbonate.

In certain embodiments, the medical device comprises (a) a first polymeric matrix region comprising a first biocompatible polymer and a therapeutic agent, and (b) a second polymer matrix region comprising a second biocompatible polymer and a radio-opacifying agent, wherein the first and second biocompatible polymers may be the same or different.

In certain embodiments, the matrix region comprises 5-20% therapeutic agent.

In certain embodiments, the therapeutic agent is ketorolac tromethamine.

In certain embodiments, the therapeutic agent is oxybutynin chloride.

In certain embodiments, the matrix region comprises 15-30% radio-opacifying agent.

In certain embodiments, the biocompatible polymer is a thermoplastic polymer.

In certain embodiments, the thermoplastic polymer is an ethylene-vinyl acetate (EVA) copolymer.

In certain embodiments, the biocompatible polymer is an elastomeric polymer.

In certain embodiments, the medical device further comprises a barrier layer.

In certain embodiments, the device further comprises an antimicrobial agent.

In certain embodiments, the implantable or insertable medical device comprises a polymeric matrix region comprising a biocompatible polymer, a therapeutic agent and a radio-opacifying agent and further comprises an antimicrobial agent.

In certain embodiments, the implantable or insertable medical device further comprises a hydrogel.

In certain embodiments, the matrix is an extruded matrix.

In certain embodiments, the extruded matrix comprises ethylene-vinyl acetate (EVA) copolymer, ketorolac tromethamine and bismuth subcarbonate.

In certain embodiments, the degradation level of the ketorotac tromethamine is less than 2%.

In accordance with another aspect of the invention, a method of manufacturing an implantable or insertable medical device like that above is provided which comprises: providing a combination comprising the biocompatible polymer and the therapeutic agent; and forming the polymeric matrix from the combination.

In certain embodiments, forming the polymeric matrix comprises a thermoplastic process.

In certain embodiments, the thermoplastic process is an extrusion process.

In certain embodiments, the thermoplastic process is conducted at a temperature that is (a) above the softening temperature of the biocompatible polymer, (b) below the melting point of the therapeutic agent, and (c) sufficiently low to avoid substantial degradation of said therapeutic agent.

In certain embodiments, the mechanical shear is further controlled to avoid such substantial degradation.

In certain embodiments, forming the polymeric matrix comprises a solution forming process.

In certain embodiments, the solution forming process is a solution coating process.

In certain embodiments, the combination further comprises a radio-opacifying agent.

In certain embodiments, forming the polymeric matrix comprises (a) forming an initial blend comprising the biocompatible polymer and the radio-opacifying agent; (b) combining the initial blend and the therapeutic agent; and (c) forming the polymeric matrix.

In certain embodiments, the initial blend is formed using a thermoplastic process.

In certain embodiments, the initial blend is formed using an extrusion process.

In certain embodiments, the polymeric matrix is formed using a further thermoplastic process.

In certain embodiments, such a further thermoplastic process is conducted under conditions such that substantial degradation of the therapeutic agent is avoided.

In certain embodiments, such a further thermoplastic process is conducted under conditions such that degradation of the therapeutic agent is less than 2%.

In certain embodiments, the initial blend is formed using a solution process and the polymeric matrix is formed using a thermoplastic process.

What is claimed is:

1. An implantable or insertable medical device comprising: a single-layer matrix polymer structure formed from a mixture comprising an extruded polymeric matrix region comprising (a) a biocompatible polymer, (b) a radio-opacifying agent, and (c) at least one therapeutic agent, wherein said medical device is adapted for implantation or insertion at a site that is associated with pain or discomfort upon implantation or insertion, wherein said radio-opacifying agent is bismuth subcarbonate, wherein said therapeutic agent is ketorolac and pharmaceutically acceptable salts thereof, and wherein said biocompatible polymer is an ethylene-vinyl acetate (EVA) copolymer.

2. The implantable or insertable medical device of claim 1, wherein said medical device comprises (a) a first extruded polymeric matrix region comprising a first biocompatible polymer and said therapeutic agent, and (b) a second extruded polymer matrix region comprising a second biocompatible polymer and said radio-opacifying agent, wherein said first and second biocompatible polymers may be the same or different.

3. The implantable or insertable medical device of claim 1, wherein said extruded polymeric matrix region comprises 5-20% therapeutic agent.

4. The implantable or insertable medical device of claim 1, wherein said therapeutic agent is ketorolac tromethamine.

5. The implantable or insertable medical device of claim 1, wherein said extruded polymeric matrix region comprises 15-30% radio-opacifying agent.

6. The implantable or insertable medical device of claim 1, further comprising a barrier layer.

7. The implantable or insertable medical device of claim 1, further comprising an antimicrobial agent.

8. The implantable or insertable medical device of claim 1, further comprising a hydrogel.

9. The implantable or insertable medical device of claim 1, wherein the extruded polymeric matrix region comprises ethylene-vinyl acetate (EVA) copolymer, ketorolac tromethamine and bismuth subcarbonate.

10. The implantable or insertable medical device of claim 9, wherein the degradation level of the ketorolac tromethamine is less than 2%.

11. A method of manufacturing an implantable or insertable medical device that comprises a polymeric matrix region comprising: (a) a biocompatible polymer, (b) at least one therapeutic agent selected from ketorolac and pharmaceutically acceptable salts thereof and (c) a radio-opacifying agent, wherein said medical device is adapted for implantation or insertion at a site that is associated with pain or discomfort upon implantation or insertion, said method comprising:

providing a combination comprising said biocompatible polymer, said therapeutic agent and said radio-opacifying agent;

extruding said combination; and forming said polymeric matrix from said combination into a single-layer matrix polymer structure, wherein said radio-opacifying agent is bismuth subcarbonate, and wherein said biocompatible polymer is an ethylene-vinyl acetate (EVA) copolymer.

12. The method of claim 11, wherein forming said polymeric matrix comprises (a) forming an initial blend comprising said biocompatible polymer and said radio-opacifying agent; (b) combining said initial blend and said therapeutic agent; and (c) forming said polymeric matrix.

13. The method of claim 12, wherein said initial blend is formed using a thermoplastic process.

14. The method of claim 12, wherein said initial blend is formed using an extrusion process.

15. The method of claim 13, wherein said polymeric matrix is formed using a further thermoplastic process.

16. The method of claim 15, wherein said further thermoplastic process is conducted under conditions such that substantial degradation of said therapeutic agent is avoided.

17. The method of claim 15, wherein said further thermoplastic process is conducted under conditions such that degradation of said therapeutic agent is less than 2%.

18. The method of claim 12, wherein said initial blend is formed using a solution process.

19. The implantable or insertable medical device of claim 1, wherein the implantable or insertable medical device is a ureteral stent.

20. The method of claim 11, wherein the implantable or insertable medical device is a ureteral stent.

21. The implantable or insertable medical device of claim 9, wherein the implantable or insertable medical device is a ureteral stent.

22. The implantable or insertable medical device of claim 1, wherein said medical device is a ureteral stent and wherein the cumulative release of therapeutic agent is in an amount selected from 5%, 10%, 15%, 20%, 25%, 30%, 40%, 50%, 60%, 70%, 80%, 90%, 95%, and 99%, relative to the total therapeutic agent in the device, after implantation or insertion at said site for a period selected from 1 day, 2 days, 4 days, 1 week, 2 weeks, 1 month, 2 months, 4 months, 1 year and 2 years.

23. The device of claim 1, further comprising a lubricious layer comprising one or more hydrogels comprising a hydrophilic polymeric material.

* * * * *

UNITED STATES PATENT AND TRADEMARK OFFICE
CERTIFICATE OF CORRECTION

PATENT NO.        : 8,133,501 B2
APPLICATION NO.   : 10/377131
DATED             : March 13, 2012
INVENTOR(S)       : Li Jianmin et al.

Page 1 of 1

It is certified that error appears in the above-identified patent and that said Letters Patent is hereby corrected as shown below:

Title Page
Attorney, Agent, or firm, (74), after "David B. Bonham" change "Kevin J. Park" to --Keum J. Park--.

Specification, col. 13, line 2, after "the" change "LC" to --ILC--.

Specification, col. 21, line 27-28, after "ureteral" change "scent" to --stent--.

Signed and Sealed this
Eighth Day of May, 2012

David J. Kappos
*Director of the United States Patent and Trademark Office*